(12) United States Patent
Wang et al.

(10) Patent No.: US 11,999,677 B2
(45) Date of Patent: Jun. 4, 2024

(54) BENZYLAMINO-OXOETHYL BENZAMIDE ANALOGS AND METHODS OF USE

(71) Applicant: The Board of Regents of the University of Oklahoma, Norman, OK (US)

(72) Inventors: Weidong Wang, Edmond, OK (US); Venkateswararao Eeda, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 298 days.

(21) Appl. No.: 17/666,692

(22) Filed: Feb. 8, 2022

(65) Prior Publication Data

US 2022/0162157 A1 May 26, 2022

Related U.S. Application Data

(63) Continuation of application No. 16/559,160, filed on Sep. 3, 2019, now abandoned.

(60) Provisional application No. 62/726,634, filed on Sep. 4, 2018.

(51) Int. Cl.
| | |
|---|---|
| *C07C 233/73* | (2006.01) |
| *A61K 31/166* | (2006.01) |
| *A61P 3/10* | (2006.01) |
| *C07C 237/22* | (2006.01) |
| *C07C 311/46* | (2006.01) |
| *C07D 213/40* | (2006.01) |
| *C07D 231/56* | (2006.01) |
| *C07D 317/54* | (2006.01) |

(52) U.S. Cl.
CPC .......... *C07C 233/73* (2013.01); *C07D 317/54* (2013.01)

(58) Field of Classification Search
CPC ... C07C 233/73; C07C 237/22; C07C 311/46; A61K 31/166; C07D 317/54; C07D 213/40; C07D 231/56; A61P 3/10
See application file for complete search history.

(56) References Cited

PUBLICATIONS

Albrecht, M., M. Napp, and M. Schneider, "The Synthesis of Amino Acid Bridged Dicatechol Derivatives", Synthesis (2001), 3: pp. 468-472. (Year: 2001).*
Bertolotti, A., et al.; "Dynamic interaction of BiP and ER stress transducers in the unfolded-protein response"; Nature Cell Biology 2 (2000) 326-332.
Kaufman, R.J., et al.; "Orchestrating the unfolded protein response in health and disease"; J. Clin. Invest. 110 (2002) 1389-1398.
Ozcan, U., et al.; "Endoplasmic Reticulum Stress Links Obesity, Insulin Action, and Type 2 Diabetes"; Science 306 (2004) 457-461.
Ozcan, U., et al.; "Chemical Chaperones Reduce ER Stress and Restore Glucose Homeostasis in a Mouse Model of Type 2 Diabetes"; Science 313:5790 (2006) 1137-1140.
Prentki, M., et al.; "Islet B cell failure in type 2 diabetes"; The Journal of Clinical Investigation 116:7 (2006) 1802-1812.
Ramalho, R.M., et al.; "Bile acids and apoptosis modulation: an emerging role in experimental Alzheimer's disease"; Trends in Molecular Science 14:2 (2007) 54-62.
Ron, D., et al.; "Signal integration in the endoplasmic reticulum unfolded protein response"; Nature Reviews; Molecular Cell Biology 8 (2007) 519-529.
Eizirik, D.L., et al.; "The Role for Endoplasmic Reticulum Stress in Diabetes Mellitus"; Endocrine Reviews 29:1 (2008) 42-61.
Vanmeer, G., et al.; "Membrane lipids: where they are and how they behave"; Nat Rev Mol Cell Biol. 9:2 (2008) 112-124.
National Center for Biotechnology Information; "PubChem Compound Summary for CID 25402970" PubChem, https://pubchem.ncbi.nlm.nih.gov/compound/25402970; accessed Mar. 25, 2021 (2009) 18 pages.
Engin, F., et al.; "Restoring endoplasmic reticulum function by chemical chaperones: an emerging therapeutic approach for metabolic diseases"; Diabetes, Obesity and Metabolism 12 (Suppl. 2) (2010) 108-115.
Fonseca, S.G., et al.; "Endoplasmic reticulum stress and pancreatic beta cell death"; Trends Endocrinal Metab. 22:7 (2011) 266-274.
Back, S.H., et al.; "Endoplasmic Reticulum Stress and Type 2 Diabetes"; Annu Rev Biochem. 81 (2012) 767-793.
STN CAS Registry Entry No. CAS RN 1385083-33-9; Entry Date: Aug. 1, 2012; 2 pages.
Papa, F.R.; "Endoplasmic Reticulum Stress, Pancreatic B-Cell Degeneration, and Diabetes"; Cold Spring Harb Perspect Med (a007666) (2012) 1-17.
Tersey, S.A., et al.; "Islet B-Cell Endoplasmic Reticulum Stress Precedes the Onset of Type 1 Diabetes in the Nonobese Diabetic Mouse Model"; Diabetes 62 (2012) 818-827.
Engin, F., et al.; "Restoration of the Unfolded Protein Response in Pancreatic B Cells Protects Mice Against Type 1 Diabetes"; Sci Transl Med. 5:211 (2013) 1-27.
Hetz, C., et al.; "Targeting the unfolded protein response in disease"; Nature Reviews; Drug Discovery 12 (2013) 703-719.
Liu, J., et al.; "Treatment of Obesity with Celastrol"; Cell. 161:5 (2015) 999-1011.
Duan, H., et al.; "Identification of 1,2,3-triazole derivatives that protect pancreatic B cells against endoplasmmic reticulum stress-mediated dysfunction and death through the inhibition of C/EBP-homologous protein expression"; Bioorg Med Chem. 24:12 (2016) 2621-2630.

(Continued)

*Primary Examiner* — Amanda L. Aguirre
*Assistant Examiner* — Sagar Patel
(74) *Attorney, Agent, or Firm* — Hall Estill Law Firm

(57) ABSTRACT

Benzylamino-oxoethyl benzamide compounds for use in treating diseases and conditions associated with abnormal cell function related to endoplasmic reticulum (ER) stress. For example, the compounds can be used as suppressors of ER stress-induced pancreatic β-cell dysfunction and death, for example in the treatment of Type 1 and Type 2 diabetes. The compounds can also be used in treatments for chronic heart disease, neurodegenerative diseases, retinal degeneration, and other metabolic disorders associated with ER stress.

4 Claims, 1 Drawing Sheet

(56) References Cited

PUBLICATIONS

Lee, J., et al.; "Withaferin A is a Leptin Sensitizer with Strong Anti-Diabetic Properties in Mice"; Nat Med. 22:9 (2016) 1023-1032.
Montane, J., et al.; "Amyloid-induced B-cell dysfunction and islet inflammation are ameliorated by 4-phenylbutyrate (PBA) treatment"; FASEB Journal 31 (2017) 5296-5306.
Nonoyama, A., et al.; "Assymetric flow catalysis: Mix-and-go solid-phase ND/NA catalyst for expeditious enantioselective access to a key intermediate of AZD7594"; Tetrahedron 73 (2017) 1517-1521.
STN CAS Registry Entry No. CAS RN 2184492-52-0; Entry Date: Mar. 5, 2018; 2 pages.
National Center for Biotechnology Information; "PubChem Bioassay Record for AID 1259397" PubChem, https://pubchem.ncbi.nim.nih.gov/bioassay/1259397; accessed Mar. 25, 2021 (2018) 12 pages.

\* cited by examiner

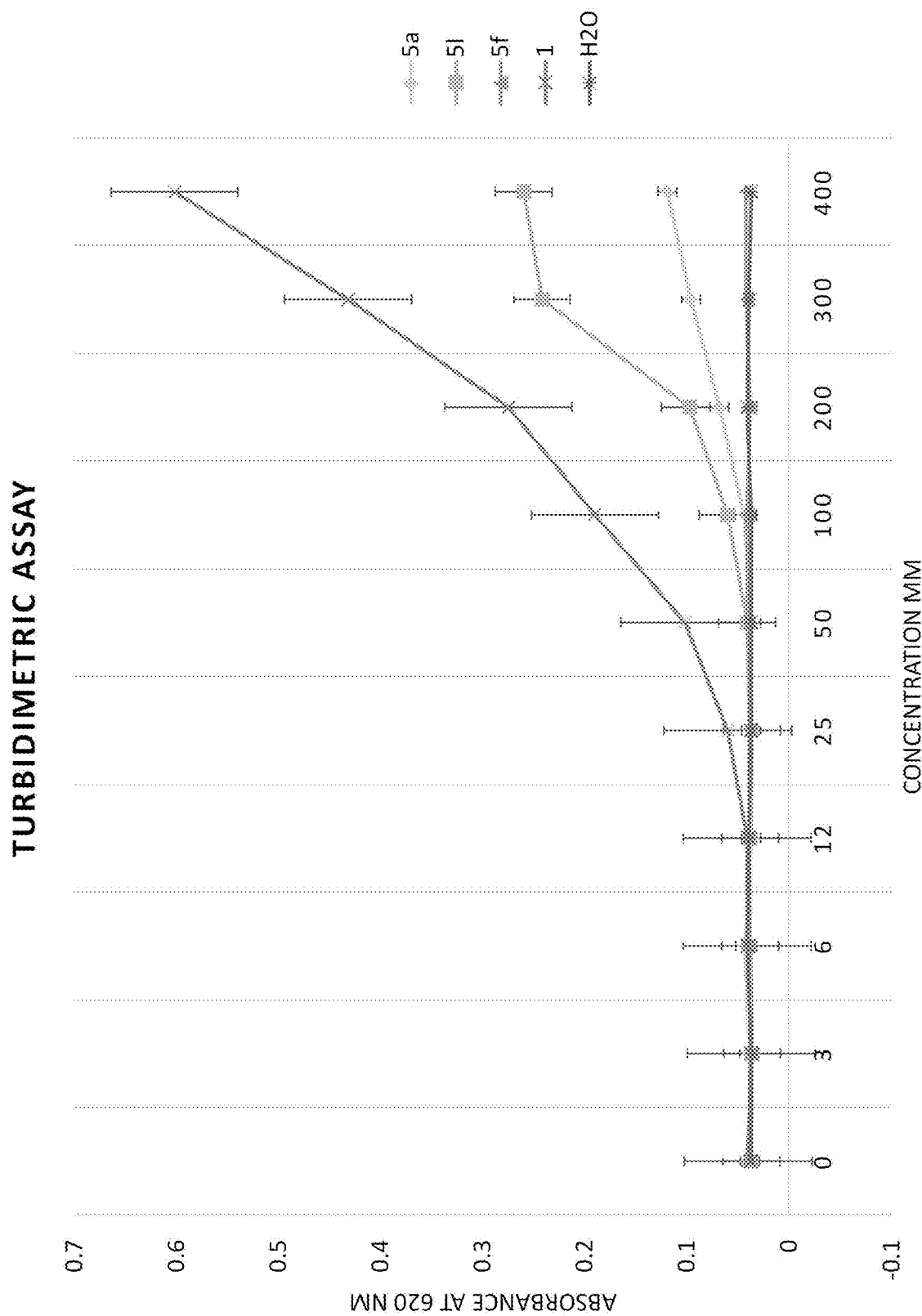

BENZYLAMINO-OXOETHYL BENZAMIDE ANALOGS AND METHODS OF USE

CROSS-REFERENCE TO RELATED APPLICATIONS

The present application is a continuation of U.S. application Ser. No. 16/559,160, filed Sep. 3, 2019, which claims priority under 35 U.S.C. § 119(e) to U.S. Ser. No. 62/726,634, filed Sep. 4, 2018, the entirety of which are hereby expressly incorporated by reference herein.

GOVERNMENT SUPPORT

This invention was made with government support under Grant numbers GM103636 and DK108887 awarded by the National Institutes of Health. The government has certain rights in the invention.

BACKGROUND

The endoplasmic reticulum (ER) has key roles in synthesis, folding and maturation of secreted transmembrane proteins. Upon translation, secretory, luminal and membrane proteins are translocated into the lumen of the ER where they are covalently modified and attain their proper folding. A balance between the ER protein loading and its folding capacity must be established to maintain the proper function of the ER. However, pathophysiological stimuli can disrupt this ER homeostasis, resulting in an accumulation of unfolded or misfolded proteins in the ER, a condition known as ER stress. ER stress triggers an evolutionarily conserved signaling cascade called the unfolded protein response (UPR). This process is mediated by three ER membrane-spanning proteins, inositol-requiring protein 1α (IRE1α), PKR-like ER kinase (PERK), and activating transcription factor 6 (ATF6), which act as unfolded protein sensors. In unstressed cells, these sensors are maintained in an inactive state through interaction with the protein chaperone binding immunoglobulin protein (BiP). Under ER stress, unfolded and misfolded proteins accumulate in the ER and bind to and sequester BiP, thereby releasing and activating the sensors. As an initial adaptive response, IRE1α, PERK, and ATF6 each activates a series of events aimed at restoring ER homeostasis by altering the translation, folding, and post-translational modification of secreted and membrane proteins. Under chronic or severe ER stress, however, the UPR often fails to adequately resolve ER stress and instead activates the expression of ER stress-specific pro-apoptotic genes such as the transcription factor C/EBP-homologous protein (CHOP), eventually leading to cell death.

Type 2 Diabetes (T2D), a chronic condition of hyperglycemia, is a pervasive threat to health and a burden on the healthcare system in the United States. T2D usually develops in obese and insulin-resistant subjects with the onset of insulin-producing R cell dysfunction and death. Increasing evidence indicates that ER stress is a major mechanism underlying the progressive decline in β cell function and mass in T2D patients. ER stress has also been implicated in T1D and monogenic diabetes. These findings illustrate the therapeutic potential for novel drugs that block ER stress-induced β cell dysfunction and death for the treatment of T1D and T2D.

Recent reports of chemical chaperones such as 4-phenyl butyrate (PBA) and tauroursodeoxycholic acid (TUDCA) have been shown to have an effect on ER stress modulation and antidiabetic activity in T2D animal models. However, because of their low efficacy, large doses are needed for any therapeutic treatment, which makes it unlikely that these agents can be used for the treatment for human patients due to the increased toxicity. Agents which are effective in treating ER stress-related conditions at low doses would be highly desirable. It is to this need that the present disclosure is directed.

BRIEF DESCRIPTION OF THE DRAWINGS

FIG. 1 shows the aqueous solubility of compounds 5a, 5f and 5l as compared to that of compound 1. Aqueous solubility was assessed as the degree of turbidity of compound in aqueous solutions, detected by absorbance at 620 nm. Higher turbidity indicated lower solubility. The experiments were performed in triplicate, with the results as the means±SD of triplicate wells.

DETAILED DESCRIPTION

Pancreatic β-cell dysfunction and death induced by Endoplasmic reticulum (ER) stress plays important roles in the development of diabetes and other conditions such as chronic heart disease, neurodegenerative diseases, retinal degeneration, and other metabolic disorders. Disclosed herein are various benzylamino-oxoethyl benzamide compounds that possess activity against ER stress and can be used, for example, as agents for protecting pancreatic β-cells against ER stress for treatment of Type 1 diabetes (T1D) and Type 2 diabetes (T2D). In other embodiments, the agents can be used in treatments for chronic heart disease, neurodegenerative diseases, retinal degeneration, and other metabolic disorders associated with ER stress. In certain non-limiting embodiments the analogs include N-(2-(Benzylamino)-2-oxoethyl)benzamide analogs.

Before further describing various embodiments of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods and application and uses thereof disclosed herein can be made and executed without undue experimentation in light of the present disclosure. Thus, while the compounds, compositions, and methods of the present disclosure have been described in terms of particular embodiments, it will be apparent to those of skill in the art that variations may be applied to the compounds, compositions, and methods and in the steps or in the sequence of steps of the methods described herein without departing from the concept, spirit, and scope of the inventive concepts.

All patents, published patent applications, and non-patent publications including published articles mentioned in the specification or referenced in any portion of this application, are herein expressly incorporated by reference in their entirety to the same extent as if each individual patent or publication was specifically and individually indicated to be incorporated by reference.

The following terms and abbreviations may be used herein: activating transcription factor 6—ATF6; binding immunoglobulin protein—BiP; 1-[Bis(dimethylamino) methylene]-1H-1,2,3-triazolo[4,5-b]pyridinium 3-oxide hexafluorophosphate—HATU; C/EBP-homologous protein—CHOP; dichloromethane—DCM; dimethyl—diMe; dimethylformamide—DMF; dimethyl sulfoxide—DMSO; endoplasmic reticulum—ER; ethanol—EtOH; ethylene dichloride—EDC; fetal bovine serum—FBS; hydrochloric acid=HCL; hydroxybenzotriazole—HOBt; 4-(2-hydroxyethyl)-1-piperazineethanesulfonic acid—HEPES; inositol-requiring protein 1α—IRE1α; insulin secreting-1 cell line—INS-1; lithium hydroxide—LiOH; megahertz—MHz; methyl—Me; methoxy—OMe; N,N-diisopropylamine—DIPEA; nuclear magnetic resonance—NMR; PKR-like ER kinase—PERK; 4-phenyl butyrate—PBA; structure-activity relationship—SAR; tauroursodeoxycholic acid—TUDCA; thin layer chromatography—TLC; tunicamycin—Tm; Type 1 diabetes—T1D; Type 2 diabetes—T2D; unfolded protein response—UPR.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds or conjugates of the present disclosure may be combined with one or more pharmaceutically-acceptable excipients, including carriers, vehicles, diluents, and adjuvents which may improve solubility, deliverability, dispersion, stability, and/or conformational integrity of the compounds or conjugates thereof.

The term "active agent" or "analog" as used herein refers to benzylamino-oxoethyl benzamide derivative compounds as described herein or active conjugates thereof. A conjugate is a compound comprising an active agent covalently linked, directly or indirectly via a linker molecule, to a secondary compound, such as an antibody or fragment thereof. The active agent may be associated with a targeting moiety or molecule which is able to bind to a target cell or a portion of a target cell. The targeting moiety may be linked directly or indirectly to the active agent, or to the pharmaceutically acceptable carrier, vehicle, or diluent which contains or is associated with the active agent. The targeting moiety may be any molecule that can bind to another molecule. For example, a targeting moiety may include an antibody or its antigen-binding fragments, a receptor molecule, a chimeric antibody molecule, or an affinity reagent. As used herein, the term "targeting moiety" refers to a structure that binds or associates with a biological moiety or fragment thereof. As noted, in some embodiments, the targeting moiety may be an antibody. In some embodiments, the targeting moiety may be a monoclonal antibody (mAB). In some embodiments, the targeting moiety may be an antibody fragment, surrogate, or variant. In some embodiments, the targeting moiety may be a protein ligand. In some embodiments, the targeting moiety may be a protein scaffold. In some embodiments, the targeting moiety may be a peptide. In some embodiments, the targeting moiety may be RNA or DNA. In some embodiments, the targeting moiety may be a RNA or DNA fragment. In some embodiments, the targeting moiety may be a small molecule ligand.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the active agent to a subject for therapeutic purposes and/or for prevention. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the active agent of the present disclosure may be designed to provide delayed, controlled, extended, and/or sustained release using formulation techniques which are well known in the art.

The term "topical" is used herein to define a mode of administration through an epithelial surface, such as but not limited to, a material that is administered by being applied externally to the eye. A non-limiting example of topical administration is through the use of eyedrops.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of the active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. Where used herein, the specific term "single" is limited to only "one". Where used herein, the pronoun "we" is intended to refer to all persons involved in a particular aspect of the investigation disclosed herein and as such may include non-inventor laboratory assistants and collaborators working under the supervision of the inventor.

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. Reference to an integer with more (greater) or less than includes any number greater or less than the reference number, respectively. Thus, for example, reference to less than 100 includes 99, 98, 97, etc., all the way down to the number one (1); and less than 10 includes 9, 8, 7, etc., all the way down to the number one (1).

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the composition, the method used to administer the active agent or composition, or the variation that exists among the study subjects. As used herein the qualifiers "about" or "approximately" are intended to include not only the exact value, amount, degree, orientation, or other qualified characteristic or value, but are intended to include some slight variations including but not limited to those due to tolerances, measuring error, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±15%, or ±14%, or ±13%, or ±12%, or ±11%, or ±10%, or ±9%, or ±8%, or ±7%, or ±6%, or ±5%, or ±4%, or ±3%, or ±2%, or ±1%, or ±0.5%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 75% of the time, at least 80% of the time, at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

By "biologically active" is meant the ability of the active agent to modify the physiological system of an organism without reference to how the active agent has its physiological effects.

Effectiveness of a method or use, such as a treatment that provides a potential therapeutic benefit or improvement of a condition or disease, can be ascertained by various methods and testing assays.

The active agents disclosed herein can be used in the treatment of type 1 and type 2 diabetes, and other diseases or conditions involving ER stress, including neurodegenerative diseases such as Parkinson's disease, amyotrophic lateral sclerosis (ALS), Alzheimer's disease (AD), Huntington's disease, and progressive supra nuclear palsy (PSP). Other indications also include metabolic syndrome including obesity, atherosclerosis, chronic heart disease, stroke, ischemia-reperfusion injury, and cancer.

The active agents of the present disclosure may be present in the pharmaceutical compositions at any concentration that allows the pharmaceutical composition to function in accordance with the present disclosure; for example, but not by way of limitation, the active agents may be present in the composition in a range having a lower level selected from 0.0001%, 0.005%, 0.001%, 0.005%, 0.01%, 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0%; and an upper level selected from 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, and 95%. Non-limiting examples of particular ranges include a range of from about 0.0001% to about 95%, a range of from about 0.001% to about 75%; a range of from about 0.005% to about 50%; a range of from about 0.01% to about 40%; a range of from about 0.05% to about 35%; a range of from about 0.1% to about 30%; a range of from about 0.1% to about 25%; a range of from about 0.1% to about 20%; a range of from about 1% to about 15%; a range of from about 2% to about 12%; a range of from about 5% to about 10%; and the like. Any other range that includes a lower level selected from the above-listed lower level concentrations and an upper level selected from the above-listed upper level concentrations also falls within the scope of the present disclosure.

Suitable carriers, vehicles, and other components that may be included in the formulation are described, for example, in *Remington: The Science and Practice of Pharmacy, 21$^{st}$ Ed. and 22$^{nd}$ Ed.* The term "pharmaceutically acceptable" means that the carrier is a non-toxic material that does not interfere with the effectiveness of the biological activity of the active agent. The characteristics of the carrier will depend on various factors, including but not limited to, the route of administration.

For example, but not by way of limitation, the active agent may be dissolved in a physiologically acceptable pharmaceutical carrier or diluent and administered as either a solution or a suspension. Non-limiting examples of suitable pharmaceutically acceptable carriers include water, saline, dextrose solutions, fructose solutions, ethanol, or oils of animal, vegetative, or synthetic origin, or any combination thereof. A sterile diluent, which may contain materials generally recognized for approximating physiological conditions and/or as required by governmental regulations, may be employed as the pharmaceutically acceptable carrier. In this respect, the sterile diluent may contain a buffering agent to obtain a physiologically acceptable pH, such as (but not limited to) sodium chloride, saline, phosphate-buffered saline, and/or other substances which are physiologically acceptable and/or safe for use.

The pharmaceutical compositions may also contain one or more additional components in addition to the active agent and pharmaceutically acceptable carrier(s) (and other additional therapeutically active agent(s), if present). Examples of additional components that may be present include, but are not limited to, diluents, fillers, salts, buffers, preservatives, stabilizers, solubilizers, and other materials well known in the art. Another particular non-limiting example of an additional component that may be present in the pharmaceutical composition is a delivery agent, as discussed in further detail herein below.

Other embodiments of the pharmaceutical compositions of the present disclosure may include the incorporation or entrapment of the active agent in various types of drug delivery systems that function to provide targeted delivery, controlled release, and/or increased half-life to the active agent. For example, but not by way of limitation, it is possible to entrap the active agent in microcapsules prepared by coacervation techniques or by interfacial polymerization (for example, hydroxymethylcellulose or gelatin-microcapsules and poly-(methylmethacylate) microcapsules, respectively). It is also possible to entrap the active agent in macroemulsions or colloidal drug delivery systems (such as but not limited to, liposomes, albumin microspheres, microemulsions, nanoparticles, nanocapsules, and the like). Such techniques are well known to persons having ordinary skill in the art, and thus no further description thereof is deemed necessary.

In one particular, non-limiting example, the pharmaceutical composition may include a liposome in which the active agent is disposed. In addition to other pharmaceutically acceptable carrier(s), the liposome may contain amphipathic agents such as lipids which exist in an aggregated form as micelles, insoluble monolayers, liquid crystals, or lamellar layers in aqueous solution. Suitable lipids for liposomal formulation include, but are not limited to, monoglycerides, diglycerides, sulfatides, lysolecithin, phospholipids, saponin, bile acids, combinations thereof, and the like. Preparation of such liposomal formulations is well within the level of ordinary skill in the art, as disclosed, for example, in U.S. Pat. Nos. 4,235,871; 4,501,728; 4,837,028; and 4,737,323; the entire contents of each of which are incorporated herein by reference.

In other non-limiting examples, the active agent of the present disclosure may be incorporated into particles of one or more polymeric materials, as this type of incorporation can be useful in controlling the duration of action of the active agent by allowing for controlled release from the preparations, thus increasing the half-life thereof. Non-limiting examples of polymeric materials that may be utilized in this manner include polyesters, polyamides, polyamino acids, hydrogels, poly(lactic acid), ethylene vinylacetate copolymers, copolymer micelles of, for example, PEG and poly(1-aspartamide), and combinations thereof.

The pharmaceutical compositions described or otherwise contemplated herein may further comprise at least one delivery agent, such as a targeting moiety, that assists in delivery of the active agent to a desired site of delivery, such as a pancreatic beta cell.

The compositions of the present disclosure may be formulated for administration by any other method known or otherwise contemplated in the art, as long as the route of administration allows for delivery of the active agent so that the compounds can function in accordance with the present disclosure, e.g., to reduce ER stress. Examples of other routes of administration include, but are not limited to, oral, topical, retrobulbar, subconjunctival, transdermal, parenteral, subcutaneous, intranasal, intramuscular, intraperitoneal, intravitreal, and intravenous routes, including both local and systemic application routes.

Another non-limiting embodiment of the present disclosure is directed to a kit that contain one or more of any of the pharmaceutical compositions described or otherwise contemplated herein. The kit may further contain a second agent as described herein above for use concurrently with the pharmaceutical composition(s). If the composition present in the kit is not provided in the form in which it is to be delivered, the kit may further contain a pharmaceutically acceptable carrier, vehicle, diluent, or other agent for mixing with the active agent for preparation of the pharmaceutical composition. The kit including the composition and/or other reagents may also be packaged with instructions packaged for administration and/or dosing of the compositions contained in the kit. The instructions may be fixed in any tangible medium, such as printed paper, or a computer-readable magnetic or optical medium, or instructions to reference a remote computer data source such as a worldwide web page accessible via the internet.

The kit may contain single or multiple doses of the pharmaceutical composition which contains the active agent. When multiple doses are present, the doses may be disposed in bulk within a single container, or the multiple doses may be disposed individually within the kit; that is, the pharmaceutical compositions may be present in the kit in unit dosage forms to facilitate accurate dosing. The term "unit dosage forms" as used herein refers to physically discrete units suitable as unitary dosages for human subjects and other mammals; each unit contains a predetermined quantity of the active agent calculated to produce the desired therapeutic effect, in association with a suitable pharmaceutical excipient. Typical unit dosage forms of liquid compositions include prefilled, premeasured ampules or syringes; for solid compositions, typical unit dosage forms include pills, tablets, capsules, or the like. In such compositions, the active agent may sometimes be a minor component (from about 0.1 to about 50% by weight, such as but not limited to, from about 1 to about 40% by weight) with the remainder being various vehicles or carriers and processing aids helpful for forming the desired dosing form.

The active agent may be provided as a "pharmaceutically acceptable salt," which refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297 (incorporated by reference herein in its entirety).

The amount of the active agent that is effective in the treatment described herein can be determined by the attending diagnostician, as one of ordinary skill in the art, by the use of conventional techniques and by observing results obtained under analogous circumstances. In determining the therapeutically effective dose, a number of factors may be considered by the attending diagnostician, including, but not limited to: the species of the subject; its size, age, and general health; the specific diseases or other conditions involved; the degree, involvement, and/or severity of the diseases or conditions; the response of the individual subject; the particular active agent administered; the mode of administration; the bioavailability characteristics of the preparation administered; the dose regimen selected; the use of concomitant medication; and other relevant circumstances. A therapeutically effective amount of an active agent of the present disclosure also refers to an amount of the active agent which is effective in controlling, reducing, or ameliorating the condition to be treated.

Practice of the method of the present disclosure may include administering to a subject a therapeutically effective amount of the pharmaceutical composition (containing the active agent in any suitable systemic and/or local formulation, in an amount effective to deliver the dosages listed above. The dosage can be administered, for example, but not by way of limitation, on a one-time basis, or administered at multiple times (for example, but not by way of limitation, from one to five times per day, or once or twice per week). The pharmaceutical composition may be administered either alone or in combination with other therapies, in accordance with the inventive concepts disclosed herein.

Compositions of the active agent can be administered in a single dose treatment or in multiple dose treatments on a schedule and over a time period appropriate to the age, weight and condition of the subject, the particular composition used, and the route of administration. In one embodiment, a single dose of the composition according to the disclosure is administered. In other embodiments, multiple doses are administered. The frequency of administration can vary depending on any of a variety of factors, e.g., severity of the symptoms, degree of immunoprotection desired, or whether the composition is used for prophylactic or curative purposes. For example, in certain embodiments, the composition is administered once per month, twice per month, three times per month, every other week, once per week, twice per week, three times per week, four times per week, five times per week, six times per week, every other day, daily, twice a day, or three times a day. The duration of treatment, e.g., the period of time over which the composition is administered, can vary, depending on any of a variety of factors, e.g., subject response. For example, the composition can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The compositions can be combined with a pharmaceutically acceptable carrier (excipient) or vehicle to form a pharmacological composition. Pharmaceutically acceptable carriers can contain a physiologically acceptable compound that acts to, e.g., stabilize, or increase or decrease the absorption or clearance rates of the pharmaceutical compositions. Physiologically acceptable carriers and vehicles can include, for example, carbohydrates, such as glucose, sucrose, or dextrans, antioxidants, such as ascorbic acid or glutathione, chelating agents, low molecular weight proteins, detergents, liposomal carriers, or excipients or other stabilizers and/or buffers. Other physiologically acceptable compounds, carriers, and vehicles include wetting agents, emulsifying agents, dispersing agents or preservatives.

When administered orally, the present compositions may be protected from digestion. This can be accomplished either by complexing the active agent with a composition to render it resistant to acidic and enzymatic hydrolysis or by packaging active agent in an appropriately resistant carrier such as a liposome, e.g., such as shown in U.S. Pat. No. 5,391,377.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. For topical, transdermal administration, the agents are formulated into ointments, creams, salves, powders and gels. Transdermal delivery systems can also include, e.g., patches. The present compositions can also be administered in sustained delivery or sustained release mechanisms. For example, biodegradeable microspheres or capsules or other biodegradable polymer configurations capable of sustained delivery of the active agent can be included herein.

For inhalation, the active agent can be delivered using any system known in the art, including dry powder aerosols, liquids delivery systems, air jet nebulizers, propellant systems, and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

The active agent can be delivered alone or as pharmaceutical compositions by any means known in the art, e.g., systemically, regionally, or locally; by intra-arterial, intrathecal (IT), intravenous (IV), parenteral, intra-pleural cavity, topical, oral, or local administration, as subcutaneous, intratracheal (e.g., by aerosol) or transmucosal (e.g., buccal, bladder, vaginal, uterine, rectal, nasal mucosa).

In one aspect, the pharmaceutical formulations comprising the active agent are incorporated in lipid monolayers or bilayers, e.g., liposomes, such as shown in U.S. Pat. Nos. 6,110,490; 6,096,716; 5,283,185; and 5,279,833. Liposomes and liposomal formulations can be prepared according to standard methods and are also well known in the art, such as U.S. Pat. Nos. 4,235,871; 4,501,728 and 4,837,028.

In one aspect, the active agent is prepared with one or more carriers that will protect the active agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The active agent in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active agent is combined in a mixture with one or more pharmaceutically suitable excipients. Sterile phosphate-buffered saline is one example of a pharmaceutically suitable excipient.

Examples of routes of administration of the active agents described herein include parenteral injection, e.g., by subcutaneous, intramuscular or transdermal delivery. Other forms of parenteral administration include intravenous, intraarterial, intralymphatic, intrathecal, intraocular, intracerebral, or intracavitary injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hanks' solution. Nonaqueous excipients such as fixed oils and ethyl oleate may also be used. An alternative excipient is 5% dextrose in saline. The excipient may contain minor amounts of additives such as substances that enhance isotonicity and chemical stability, including buffers and preservatives.

Formulated compositions comprising the active agent can be used for subcutaneous, intramuscular or transdermal administration. Compositions can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The active agents may be administered in solution. The formulation thereof may be in a solution having a suitable pharmaceutically acceptable buffer such as phosphate, Tris (hydroxymethyl) aminomethane-HCl or citrate, and the like. Buffer concentrations should be in the range of 1 to 100 mM. The formulated solution may also contain a salt, such as sodium chloride or potassium chloride in a concentration of 50 to 150 mM. An effective amount of a stabilizing agent such as mannitol, trehalose, sorbitol, glycerol, albumin, a globulin, a detergent, a gelatin, a protamine or a salt of protamine may also be included.

For example, but not by way of limitation, the therapeutically effective amount of an active agent used in the present disclosure will generally contain sufficient active agent to deliver in a range of from about 0.01 µg/kg to about 10 mg/kg (weight of active agent/body weight of patient). For example, but not by way of limitation, the composition will deliver about 0.1 µg/kg to about 5 mg/kg, and more particularly about 1 µg/kg to about 1 mg/kg.

Exemplary, non-limiting ranges for a therapeutically or prophylactically effective amount of the active agent include but are not limited to 0.001 mg/kg of the subject's body weight to 100 mg/kg of the subject's body weight, more typically 0.01 mg/kg to 100 mg/kg, 0.1 mg/kg to 50 mg/kg, 0.1 mg/kg to 40 mg/kg, 1 mg/kg to 30 mg/kg, or 1 mg/kg to 20 mg/kg, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg, or 5 mg to 1500 mg, as a fixed dosage.

The composition is formulated to contain an effective amount of the active agent, wherein the amount depends on the animal to be treated and the condition to be treated. In certain embodiments, the active agent is administered at a dose ranging from about 0.001 mg to about 10 g, from about 0.01 mg to about 10 g, from about 0.1 mg to about 10 g, from about 1 mg to about 10 g, from about 1 mg to about 9 g, from about 1 mg to about 8 g, from about 1 mg to about 7 g, from about 1 mg to about 6 g, from about 1 mg to about 5 g, from about 10 mg to about 10 g, from about 50 mg to about 5 g, from about 50 mg to about 5 g, from about 50 mg to about 2 g, from about 0.05 µg to about 1.5 mg, from about 10 µg to about 1 mg protein, from about 30 µg to about 500 µg, from about 40 pg to about 300 pg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy.

The dosage of an administered active agent for humans will vary depending upon such factors as the patient's age, weight, height, sex, general medical condition and previous medical history. In certain non-limiting embodiments, the recipient is provided with a dosage of the active agent that is in the range of from about 1 mg to 1000 mg as a single infusion or single or multiple injections, although a lower or higher dosage also may be administered. The dosage may be in the range of from about 25 mg to 100 mg of the active agent per square meter ($m^2$) of body surface area for a typical adult, although a lower or higher dosage also may be administered. Examples of dosages that may be administered to a human subject further include, for example, 1 to 500 mg, 1 to 70 mg, or 1 to 20 mg, although higher or lower doses may be used. Dosages may be repeated as needed, for example, once per week for 4-10 weeks, or once per week for 8 weeks, or once per week for 4 weeks. It may also be given less frequently, such as every other week for several months, or more frequently, such as twice weekly or by continuous infusion.

Where used herein alkyls, alkoxyls, haloalkyls, and haloalkoxyls are generally intended to refer to molecules having hydrocarbon chains that comprise 1, 2, 3, 4, 5, 6, 7, 8, 9, 10, 11, or 12 carbons, unless otherwise designated. The hydrocarbon chains may be straight or branched. Examples of alkyls include but are not limited to methyl, ethyl, propyl, isopropyl, and butyl. Alkoxy denotes an alkyl group which is linked to an oxygen atom. Examples of alkoxyls include but are not limited to methoxyl, ethoxyl, propoxyl, isopropoxyl, and butoxyl. Haloalkyls and haloalkoxyls are alkyls and alkoxyls which comprise at least one halogen atom such as chlorine, fluorine, bromine, or iodine.

In at least certain embodiments, the present disclosure includes compounds and methods of treating disorders and conditions related to ER stress, including, but not limited to type 1 diabetes and type 2 diabetes (or others ER stress-related disorders or conditions described elsewhere herein including neurodegenerative diseases such as Parkinson's disease, amyotrophic lateral sclerosis (ALS), Alzheimer's disease (AD), Huntington's disease, and progressive supra nuclear palsy (PSP), metabolic syndrome including obesity, atherosclerosis, chronic heart disease, stroke, ischemia-reperfusion injury, and cancer). The compound may be an benzylamino-oxoethyl benzamide derivative compound having the chemical structure I:

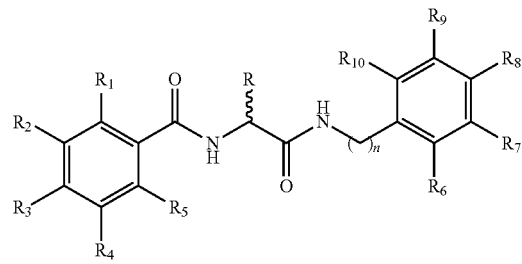

wherein:
R=H, Alkyl, or Phenyl;
$R_1$=H, Me, Cl, F, OMe, OH, or Phenyl;
$R_2$=H, Me, Cl, F, OMe, OH, or Phenyl;
$R_3$=H, $NH_2$, Me, Cl, F, OMe, OH, or Phenyl;
$R_4$=H, Me, Cl, F, OMe, OH, or Phenyl;
$R_5$=H, Me, Cl, F, OMe, or OH;
$R_6$=H, Me, Cl, F, OMe, OH, $CCl_3$, or $CF_3$;
$R_7$=H, Me, Cl, F, OMe, OH, or Piperonyl;
$R_8$=H, Me, Cl, F, OMe, OH, $CCl_3$, $CF_3$, or Piperonyl;
$R_9$=H, Me, Cl, F, or OMe;
$R_{10}$=H, Me, Cl, F, OMe, OH, $CCl_3$, or $CF_3$; and
n=0, 1, 2, or 3.

EXAMPLES

Certain novel embodiments of the present disclosure, having now been generally described, will be more readily understood by reference to the following examples, which are included merely for purposes of illustration of certain aspects and embodiments of the present disclosure, and are not intended to be limiting. The following detailed examples are to be construed, as noted above, only as illustrative, and not as limiting of the present disclosure in any way whatsoever. Those skilled in the art will promptly recognize appropriate variations from the various compositions, structures, components, procedures and methods.

Methods

Synthesis of Analogs

Synthesis of N-(2-(Benzylamino)-2-oxoethyl)benzamide 5a-q analogs is outlined in Scheme 1 and substituents of the various analogs are listed in Table 1. Commercially available substituted benzoic acids 2 were coupled with corresponding substituted ethyl glycinates 3 in the presence of EDC/HOBt in dimethylformamide to yield benzoylglycine ester, which was hydrolyzed with an aqueous solution of LiOH in ethanol at 5-10° C. afforded key intermediate benzoylglycine 4. For preparation of 5a-q analogs, benzoylglycines 4 were reacted with various substituted benzyl amine in DCM using HATU at 0-rt yielded N-(2-(Benzylamino)-2-oxoethyl)benzamide 5 analogs in excellent yields. The synthesized compounds are listed in Table 1 and characterized by physical and spectral analysis data that confirmed their assigned structures.

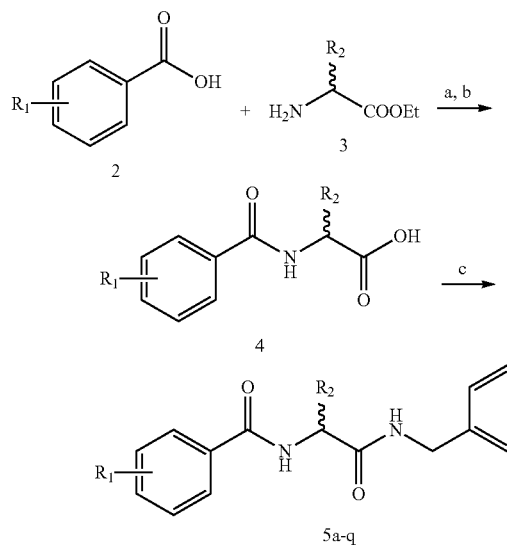

Scheme 1. Synthesis of compounds 5a-q.

Reagents & Conditions: a) HOBT, EDC, DIPEA, DMF at 0-rt; b) LiOH/EtOH 0-rt; c) HATU, DIPEA/DCM.

All commercial chemicals were used as obtained and all solvents were purified by the standard procedures prior to use. Flash column chromatography was performed with E Merck silica gel (230-400 mesh). NMR spectra were measured against the peak of tetramethylsilane by Varain Unity Inova 400 NMR (400 MHz) spectrometers.

General Procedure for the Synthesis of (4)

To a stirred solution of substituted benzoic acid (1 equivalent) in dimethylformamide was added EDC (1 equivalent), HOBt (1 equivalent) cooled to 0-5° C. and added DIPEA (2 equivalents) stirred for 10 min at same temperature. After 10 min, appropriate amine (1 equivalent) was dropwise added and continued stirring for overnight. After TLC confirmation, the reaction mixture was evaporated and the residue was extracted with ethyl acetate and washed with water. The organic layer was dried over anhydrous sodium sulfate. Solvent was removed under vacuum to provide crude residue which was purified by flash column chromatography. For hydrolysis, the ester derivative residue was dissolved in 10% aqueous ethanol. Two equivalents of LiOH dissolved in water was added to the reaction mixture and vigorously stirred for 5 h. After completion of the reaction, The reaction solvent was evaporated and acidified with 1N HCl and filtered to collect the desired compound (4) as a white solid (66%).

General Procedure for the Synthesis of (5):

To a mixture of the acid (1 equivalent) in DCM was added DIPEA (3 equivalents) and HATU (1 equivalents). The mixture was stirred for 5 min, and then the appropriate amine (1 equivalents) was added. The reaction mixture was stirred at rt for 30 min. The completion of the reaction was monitored by TLC. The solvent was removed in vacuo to obtain the crude which was purified by flash chromatography to provide product (78%).

TABLE 1

Effects of compounds 5a-q on CHOP-Luc reporter and β cell viability against Tm.

5a-b and 5g-q: n = 1;
5c: n = 0; 5f: n = 2;

| Compound ID | $R_1$ | $R_2$ | $R_3$ | Max Activity (%)[a] | $EC_{50}$ (μM)[b] |
|---|---|---|---|---|---|
| 5a | 3-Cl, 2-Me | H | 2,5-di Me | 45 | 18 ± 4 |
| 5b | 3-Cl, 2-Me | H | 2-Pyridine | 16 | 38 ± 9 |
| 5c | 3-Cl, 2-Me | H | Indazole | Cytotoxic | — |
| 5d | 3-Cl, 2-Me | H | 4-OMe | 55 | 32 ± 7 |
| 5e | 3-Cl, 2-Me | H | 4-$SO_2NH_2$ | 52 | 40 ± 12 |
| 5f | 3-Cl, 2-Me | H | Tyramine | 41 | 34 ± 8 |
| 5g | 3-Cl, 2-Me | H | 4-$CF_3$ | 88 | 13 ± 1 |
| 5h | 3-Cl, 2-Me | H | 3-OMe, 4-OH | 100 | 10 ± 2 |
| 5i | 3-Cl, 2-Me | H | 3-$CF_3$ | 46 | 32 ± 7 |
| 5j | H | H | 4-$CF_3$ | 35 | 43 ± 11 |
| 5k | 4-Et | H | 4-$CF_3$ | 42 | 45 ± 8 |
| 5l | 4-F | H | 4-$CF_3$ | 12 | 41 ± 6 |
| 5m | 3-OH | H | 4-$CF_3$ | 100 | 0.1 ± 0.01 |
| 5n | 3-OH | H | 3-OMe, 4-OH | 30 | 65 ± 8 |
| 5o | 3-OMe, 4-OH | H | 4-$CF_3$ | 43 | 29 ± 6 |
| 5p | 3-Cl, 2-Me | Me | 4-$CF_3$ | 34 | 63 ± 4 |
| 5q | 3-Cl, 2-Me | Tyrosine | 4-$CF_3$ | Cytotoxic | — |

[a]Maximum activity value is reported as % rescue from Tm (0.15 lag/mL)—induced reduction of cell viability, as measured by intracellular ATP levels; the values for Tm treatment alone and control (DMSO, without Tm) treatment are designated as 0% and 100%, respectively.
[b]$EC_{50}$ values (the concentrations that reach half-maximal activity) for INS-1 cell viability are calculated with GraphPad Prism from the data of ten 2-fold serial titration points in all tables. All experiments were performed in triplicate.

Cell Culture

INS-1 cells were cultured in RPMI 1640 medium (Corning) supplemented with 10% FBS (Atlanta Biologicals), 10 mM HEPES (Gibco-Life Technologies), 1 mM sodium pyruvate (Corning), 50 μM 2-mercaptoethanol (Sigma-Aldrich), and antibiotics (100 UI/mL penicillin and 100 pg/mL streptomycin; Corning) and maintained in a humidified 5% $CO_2$ atmosphere at 37° C.

Cell Viability Assay

INS-1 cells were resuspended in RPMI 1640 medium containing 10% FBS and plated at 5×10³ cells/(40 μL.well) into white clear bottom 384-well plates (Greiner) using an automated liquid handler (Biotek). After 24 h incubation at 37° C., library compounds were added to the wells at the indicated concentration using a pin-transfer robot (PerkinElmer). Tunicamycin (Tm) in RPMI 1640 medium containing 10% FBS was then added at a final concentration of 0.15 μg/mL. After 72 h, the medium was removed and 20 μL of CellTiter-Glo reagent which measures intracellular ATP levels as an indicator of viability (Promega) was added. Luminescence was measured 10 min later using an Envision plate reader (PerkinElmer).

Solubility Assay

Each compound was prepared at concentrations from 40 mM to 0.1 mM in DMSO in a serial-dilution manner. 2 μL of each of the above compound solutions was then dispensed directly to ~198 μL of pure $H_2O$ in a 96-well white clear bottom microplate. Resulting solutions were shaken at 37° C. temperature 1-2 h on a rotary shaker at varying shaking rates to reach equilibrium solubility. The turbidity of the solution was measured using UV-visible spectrophotometry at 620 nm. The solubility data are presented in FIG. 1.

Results

The compound 1-(3-chloro-2-methylphenyl)-N-(2,5-dimethylphenyl)-5-methyl-1H-1,2,3-triazole-4-carboxamide (1) was previously shown to have protective activity for pancreatic β-cells against ER stress. However, 1 showed less-desired potency within a narrow range of doses, and suboptimal aqueous solubility (see FIG. 1). We designed and synthesized novel benzylamino-oxoethyl benzamide analogs (5a-q, Table 1) and studied their effects on β-cell protection against ER stress. The analogs were tested for the viability of rat INS-1 β-cells in the presence of Tm, a potent ER stress inducer that inhibits N-linked glycosylation of proteins. The maximum activities and the concentrations that reach half-maximal activity ($EC_{50}$) of the compounds were evaluated by the degree of increase in viability of INS-1 cells co-treated with the compounds in the presence of Tm compared with Tm treatment alone.

Compound 5a exhibited moderate activity (maximum activity=45%, $EC_{50}$=18.6 ± 4 μM). With this encouraging result, we explored the effect of substituents on the moieties on β-cell protection. We started investigating the effect of modifying the right ring ($R_3$) on the 5a scaffold. We found that the glycine derivatives with modifications as 2-pyridine (5b) or indazole (5c) are not or minimally active (maximal activity at 16% and 0%, respectively), while derivatives with modifications as 4-OMe (5d), 4-$SO_2NH_2$ (5e), or tyramine (5f) are moderately active with maximal activity from 41 to 55%, suggesting that the introduction of new hydrogen bonding groups and the extension of length in-between amide and B-ring may are not beneficial for the activity. However, excitingly, substitutions with 4-$CF_3$ (5g) or 4-OH, 3-OMe (5h) yielded very active compounds with maximal activity at 88% and 100%, respectively, although the $EC_{50}$s of both derivatives are still less desired (13±1 and 10±2 μM, respectively). Next, as 5g showed significant β-cell protective activity (see Table 1), to establish the suitable position of the —$CF_3$ group in the phenyl ring (benzylamino) of 5g, we synthesized 5i with the —$CF_3$ group at position 3 and observed that 5i (with 3-$CF_3$) was less potent than 5g (with 4-$CF_3$) (5i with maximum activity=46%, $EC_{50}$=32±7 μM vs. 5g with maximum activity=88%, $EC_{50}$=13±1 μM). These results indicate that the $CF_3$ substitution at position 4 on phenyl ring (5g) is more favorable than at position 3 (5i) for β-cell protective activity. We therefore kept the 4-$CF_3$ substitution on the right ring for further structure-activity relationship (SAR) studies.

We next sought to determine the suitable substituents on the left (benzamide) ring ($R_1$) on β-cell protection against ER stress. The compounds synthesized with various substituents at the left ring (5j-n) are listed in Table 1. While substituting the 3-Cl, 2-Me (5g) on the phenyl ring $R_1$ with hydrogen (5j), 4-ethyl (5k), or 4-F (5l) substantially reduced their respective activities (maximal activity: 88% (5g) vs. 35% (5j), 42% (5k), or 12% (5l), and $EC_{50}$ (μM): 13±1 (5a) vs. 43±11 (5j), 45±8 (5k), or 41±6 (5l)), substitution with 3-hydroxy group (5m) remarkably enhanced the activity with the maximum activity at 100% and $EC_{50}$=0.1 ± 0.01 μM. These results suggest that the electron donating group at meta position of $R_1$ is important for the β-cell protective activity. As we have shown that compound 5h with the 3-OMe, 4-OH substituent at $R_3$ in a scaffold containing a 3-Cl, 2-Me moieties at $R_1$ exhibited the excellent β-cell protective activity, and that the 3-OH substituent (5m) at $R_1$ yielded an activity superior to that of 3-Cl, 2-Me moieties (5g) in a scaffold with 4-$CF_3$ at $R_3$, we wondered whether an analog containing 3-OH at $R_1$ and 3-OMe, 4-OH at $R_3$ (5n) and a second analog containing 3-OMe, 4-OH at $R_1$ with 4-$CF_3$ at $R_3$ (5o) are equally active. However, as shown in Table 1, these analogs exhibited a significantly compromised activity. To further explore the SAR, we studied the effect of substituent at $R_2$ position, compounds 5p ($R_2$=Me) and 5q ($R_2$=tyrosine) are significantly less or not active. These results indicated that the bulkier substitution at $R_2$ position is not well tolerated.

A major drawback to the therapeutic use of compound 1 is its poor water solubility. We investigated whether the compounds of the present disclosure have improved aqueous solubility. Using a thermodynamic turbidimetric assay we evaluated the aqueous solubility of several of the newly synthesized compounds. As shown in FIG. 1, several compounds including 5g, 5h, and 5m exhibited improved water solubility in comparison to 1.

General Procedure and Characterization of Compounds 5a-5q:

3-Chloro-N-(2-((2,5-dimethylbenzyl)amino)-2-oxoethyl)-2-methylbenzamide (5a)

The title compound was prepared following general procedures B: off-white powder. 1H NMR (CDCl$_3$, 400 MHz) δ: 7.50 (d, J=7.8 Hz, 1H), 7.41 (d, J=7.8 Hz, 1H), 7.19 (m, 3H), 7.14 (t, J=7.7 Hz, 1H), 6.97 (bs, 1H), 6.76 (bs, 1H), 4.50 (d, J=5.7 Hz, 2H), 4.17 (d, J=5.0 Hz, 2H), 2.37 (s, 3H), 2.29 (s, 6H). $^{13}$C NMR (100 MHz, CDCl$_3$) δ: 171.0, 167.9, 156.5, 148.1, 139.6, 136.8, 132.5, 132.1, 127.2, 125.5, 128.5, 127.2, 125.4, 124.1, 120.9, 48.3, 43.3, 21.6, 18.9, 17.2.

3-Chloro-2-methyl-N-(2-oxo-2-((pyridin-2-ylmethyl)amino)ethyl)benzamide (5b)

The title compound was prepared following general procedures B: a brown solid. 1H NMR (CDCl$_3$, 400 MHz) δ: 8.54 (d, J=7.8 Hz, 1H), 7.43 (d, J=7.8 Hz, 2H), 7.24 (m, 3H), 7.14 (t, J=7.7 Hz, 1H), 6.97 (bs, 1H), 6.76 (bs, 1H), 4.51 (d, J=5.7 Hz, 2H), 4.17 (d, J=5.0 Hz, 2H), 2.37 (s, 3H). $^{13}$C NMR (100 MHz, CDCl$_3$) δ:171.0, 167.9, 156.5, 148.1, 139.6, 136.8, 132.5, 132.1, 127.2, 125.5, 128.5, 127.2, 125.4, 124.1, 120.9, 48.3, 43.3, 17.2.

N-(2-((1H-benzo[d]imidazol-6-yl)amino)-2-oxoethyl)-3-chloro-2-methylbenzamide (5c)

The title compound was prepared following general procedures B: a white powder. 1H NMR (DMSO-d$_6$, 400 MHz) δ: 12.89 (s, 1H), 10.19 (s, 1H), 8.90 (t, J=5.7 Hz 1H), 8.12 (s, 1H), 7.90 (m, 3H), 7.67 (d, J=8.7 Hz, 1H), 7.33 (t, J=8.5 Hz 2H), 7.12 (d, J=8.6 Hz 1H), 4.10 (d, J=5.6 Hz, 2H), 2.35 (s, 3H). $^{13}$C NMR (100 MHz, DMSO-d$_6$) δ: 168.5, 167.1, 142.0, 138.6, 136.8, 136.7, 135.2, 134.4, 134.4, 132.7, 127.2, 123.7, 115.8, 109.5, 43.8, 17.1.

3-Chloro-N-(2-((4-methoxybenzyl)amino)-2-oxoethyl)-2-methylbenzamide (5d)

The title compound was prepared following general procedures B: a white powder. 1H NMR (DMSO-$d_6$, 400 MHz) δ: 8.86 (bs, 1H), 8.19 (bs, 1H), 7.85 (d, J=7.7 Hz, 1H), 7.66 (d, J=7.6 Hz, 1H), 7.47 (t, J=7.2 Hz, 1H), 7.22 (d, J=7.8 Hz, 2H), 6.89 (d, J=7.8 Hz, 2H), 4.23 (d, J=5.6 Hz, 2H), 4.09 (d, J=5.6 Hz, 2H), 3.81 (s, 3H), 2.33 (s, 3H). $^{13}$C NMR (100 MHz, DMSO-$d_6$) δ: 169.3, 168.2, 158.8, 137.3, 136.8, 134.4, 132.7, 132.1, 130.8, 130.2, 128.8, 127.2, 125.7, 124.4, 123.6, 123.1, 55.8, 43.9, 43.6, 17.2.

3-Chloro-2-methyl-N-(2-oxo-2-((4-sulfamoylbenzyl)amino)ethyl)benzamide (5e)

The title compound was prepared following general procedures B: a white powder. 1H NMR (DMSO-$d_6$, 400 MHz) δ: 8.80 (bs, 1H), 8.56 (bs, 1H), 7.64 (m, 3H), 7.55 (d, J=7.8 Hz, 2H), 7.48 (d, J=7.8 Hz, 2H), 7.41 (d, J=7.8 Hz, 1H), 7.14 (t, J=7.7 Hz, 1H), 4.33 (d, J=5.7 Hz, 2H), 4.09 (d, J=5.0 Hz, 2H), 2.37 (s, 3H). $^{13}$C NMR (100 MHz, DMSO-$d_6$) δ:171.0, 167.9, 156.5, 148.1, 139.6, 136.8, 132.5, 132.1, 127.2, 125.5, 128.5, 127.2, 125.4, 124.1, 120.9, 48.3, 43.3, 17.2.

3-Chloro-N-(2-((4-hydroxyphenethyl)amino)-2-oxoethyl)-2-methylbenzamide (5f)

The title compound was prepared following general procedures B: a white powder. 1H NMR (DMSO-$d_6$, 400 MHz) δ: 9.63 (s, 1H), 8.59 (bs, 1H), 8.55 (bs, 1H), 7.65 (d, J=7.7 Hz, 1H), 7.60 (d, J=7.8 Hz, 1H), 7.47 (t, J=7.6 Hz, 1H), 7.34 (d, J=7.4 Hz, 2H), 7.19 (d, J=7.4 Hz, 2H), 4.15 (d, J=5.6 Hz, 2H), 3.67 (t, J=5.8 Hz, 2H), 2.94 (t, J=5.6 Hz, 2H), 2.35 (s, 3H). $^{13}$C NMR (100 MHz, DMSO-$d_6$) δ: 167.1, 163.0, 155.0, 136.8, 134.4, 134.4, 132.1, 130.2, 127.2, 125.4, 115.8, 43.8, 40.4, 35.1, 17.1.

3-Chloro-2-methyl-N-(2-oxo-2-((4-(trifluoromethyl)benzyl)amino)ethyl)benzamide (5g)

The title compound was prepared following general procedures B: a white powder. 1H NMR (CDCl$_3$, 400 MHz) δ: 7.56 (d, J=7.8 Hz, 2H), 7.43 (d, J=7.8 Hz, 1H), 7.37 (d, J=7.9 Hz, 2H), 7.22 (s, 1H), 7.14 (t, J=7.7 Hz, 1H), 6.97 (bs, 1H), 6.76 (bs, 1H), 4.51 (d, J=5.7 Hz, 2H), 4.17 (d, J=5.0 Hz, 2H), 2.37 (s, 3H). $^{13}$C NMR (100 MHz, CDCl$_3$) δ: 171.0, 167.9, 141.1, 136.8, 134.6, 132.5, 132.1, 130.5, 129.0, 128.5, 127.2, 125.4, 124.9, 43.9, 17.2.

3-Chloro-N-(2-((4-hydroxy-3-methoxybenzyl)amino)-2-oxoethyl)-2-methylbenzamide (5h)

The title compound was prepared following general procedures B: a white powder. 1H NMR (DMSO-$d_6$, 400 MHz) δ: 8.82 (s, 1H), 8.59 (t, J=5.7 Hz, 1H), 8.30 (t, J=5.6 Hz, 1H) 7.49 (d, J=7.7 Hz, 1H), 7.34 (d, J=7.4 Hz, 1H) 7.26 (t, J=7.6 Hz, 1H) 6.85 (s, 1H), 6.68 (m, 2H), 4.20 (d, J=5.6 Hz, 2H) 3.86 (d, J=5.8 Hz, 2H), 3.74 (s, 3H), 2.35 (s, 3H). $^{13}$C NMR (100 MHz, DMSO-$d_6$) δ: 169.1, 168.9, 147.9, 145.8, 139.8, 134.6, 133.5, 130.5, 130.2, 127.5, 126.4, 120.16, 115.6, 112.1, 56.0, 42.8, 42.4, 17.1.

3-Chloro-2-methyl-N-(2-oxo-2-((3-(trifluoromethyl)benzyl)amino)ethyl)benzamide (5i)

The title compound was prepared following general procedures B: a white powder. 1H NMR (DMSO-$d_6$, 400 MHz) δ: 8.86 (bs, 1H), 8.19 (bs, 1H), 7.85 (d, J=7.7 Hz, 1H), 7.66 (d, J=7.6 Hz, 1H), 7.47 (m, 4H), 4.23 (d, J=5.6 Hz, 2H), 4.09 (d, J=5.6 Hz, 2H), 2.33 (s, 3H). $^{13}$C NMR (100 MHz, DMSO-$d_6$) δ: 170.1, 167.6, 137.3, 136.8, 134.4, 132.7, 132.1, 130.8, 130.2, 128.8, 127.2, 125.7, 124.4, 123.6, 123.1, 43.9, 43.6, 17.2.

N-(2-Oxo-2-((4-(trifluoromethyl)benzyl)amino)ethyl)benzamide (5j)

The title compound was prepared following general procedures B. 1H NMR (DMSO-$d_6$, 400 MHz) δ: 8.59 (bs, 1H), 8.30 (bs, 1H) 7.49 (m, 5H), 7.34 (d, J=7.4 Hz, 2H) 7.26 (d, J=7.6 Hz, 2H) 4.21 (d, J=5.6 Hz, 2H) 3.85 (d, J=5.8 Hz, 2H); $^{13}$C NMR (100 MHz, DMSO-$d_6$) δ: 170.1, 167.8, 147.9, 145.8, 139.8, 134.6, 133.5, 130.5, 130.2, 127.5, 126.4, 120.16, 115.6, 112.1, 56.0, 43.9, 43.3.

4-Ethyl-N-(2-oxo-2-((4-(trifluoromethyl)benzyl)amino)ethyl)benzamide (5k)

The title compound was prepared following general procedures B: a white Solid. 1H NMR (DMSO-$d_6$, 400 MHz) δ: 8.57 (t, J=5.7 Hz, 1H), 8.31 (t, J=5.6 Hz, 1H), 7.49 (m, 4H), 7.31 (d, J=8.0 Hz, 2H), 7.34 (d, J=7.4 Hz, 2H), 4.18 (d, J=5.6 Hz, 2H) 3.56 (d, J=5.8 Hz, 2H), 2.73 (q, J=7.5 Hz, 2H), 1.29 (t, J=7.5 Hz, 3H). $^{13}$C NMR (100 MHz, DMSO-$d_6$) δ: 169.0, 167.1, 147.7, 145.8, 139.8, 134.6, 133.5, 130.5, 130.2, 127.5, 126.4, 120.16, 115.6, 112.1, 56.0, 43.9, 43.3, 28.2, 14.5.

4-fluoro-N-(2-oxo-2-((4-(trifluoromethyl)benzyl)amino)ethyl)benzamide (5l)

The title compound was prepared following general procedures A: a white powder. 1H NMR (DMSO-$d_6$, 400 MHz) δ: 8.88 (s, 1H), 8.12 (s, 1H), 7.67 (d, J=8.1 Hz, 2H), 7.54 (d, J=7.9 Hz 2H), 7.37 (m, 4H), 4.19 (d, J=5.6 Hz, 2H), 4.09 (d, J=5.5 Hz, 2H), $^{13}$C NMR (100 MHz, DMSO-$d_6$) δ: 170.5, 167.1, 166.3, 141.2, 129.8, 129.1, 129.0, 128.5, 124.9, 115.8, 43.8, 43.3.

3-Hydroxy-N-(2-oxo-2-((4-(trifluoromethyl)benzyl)amino)ethyl)benzamide (5m)

The title compound was prepared following general procedures B: a white powder. 1H NMR (DMSO-$d_6$, 400 MHz) δ: 9.65 (s, 1H), 8.80 (s, 1H), 8.64 (t, J=5.4 Hz, 1H), 8.28 (t, J=5.6 Hz, 1H) 7.27 (m, 3H), 6.91 (d, J=7.2 Hz, 1H), 6.83 (s, 1H), 6.67 (m, 2H) 4.18 (d, J=5.6 Hz, 2H) 3.85 (d, J=5.8 Hz, 2H), $^3$C NMR (100 MHz, DMSO-$d_6$) δ: 169.3, 166.9, 157.7, 147.8, 145.7, 135.9, 130.6, 129.6, 129.0, 120.0, 118.6, 118.3, 115.5, 114.8, 112.0, 43.3, 42.0.

3-Hydroxy-N-(2-((4-hydroxy-3-methoxybenzyl)amino)-2-oxoethyl)benzamide (5n)

The title compound was prepared following general procedures B: a white powder. 1H NMR (DMSO-$d_6$, 400 MHz) δ: 9.86 (s, 1H), 8.79 (s, 1H), 8.63 (t, J=5.4 Hz, 1H), 8.32 (t, J=5.6 Hz, 1H) 7.27 (m, 3H), 6.91 (d, J=7.2 Hz, 1H), 6.83 (s, 1H), 6.67 (m, 2H) 4.18 (d, J=5.6 Hz, 2H) 3.85 (d, J=5.8 Hz, 2H), 3.74 (s, 3H), $^{13}$C NMR (100 MHz, DMSO-$d_6$) δ: 169.3, 166.9, 157.7, 147.8, 145.7, 135.9, 130.6, 129.6, 120.0, 118.6, 118.3, 115.5, 114.8, 112.1, 55.9, 43.6, 42.2.

4-hydroxy-3-methoxy-N-(2-oxo-2-((4-(trifluoromethyl)benzyl)amino)ethyl)benzamide (5o)

The title compound was prepared following general procedures B: White Solid. 1H NMR (DMSO-$d_6$, 400 MHz) δ: 9.89 (s, 1H), 8.87 (s, 1H), 8.24 (s, 1H), 7.54 (d, J=7.7 Hz, 2H), 7.34 (d, J=7.4 Hz, 1H) 7.32 (s, 1H), 7.26 (m, 3H) 4.22 (d, J=5.6 Hz, 2H), 4.09 (d, J=5.5 Hz, 2H), 3.74 (s, 3H). $^{13}$C NMR (100 MHz, DMSO-$d_6$) δ: 170.1, 167.9, 152.2, 151.0, 139.8, 129.0, 128.5, 126.4, 120.1, 117.6, 115.1, 56.1, 43.9, 43.3.

3-Chloro-2-methyl-N-(1-oxo-1-((4-(trifluoromethyl)benzyl)amino)propan-2-yl)benzamide (5p)

The title compound was prepared following general procedures B: off-white powder. 1H NMR (DMSO-$d_6$, 400 MHz) δ: 8.51 (m, 2H), 7.68 (d, J=7.9 Hz, 2H), 7.49 (d, J=8.2 Hz, 3H) 7.28 (m, 2H), 4.41 (m, 3H), 2.31 (s, 3H), 1.32 (d, J=7.0 Hz, 3H). $^{13}$C NMR (100 MHz, DMSO-$d_6$) δ: 171.0, 167.9, 141.2, 136.8, 134.4, 132.9, 132.1, 129.0, 128.5, 127.2, 124.9, 124.1, 54.9, 43.6, 17.9, 17.2.

3-Chloro-N-(3-(4-hydroxyphenyl)-1-oxo-1-((4-(trifluoromethyl)benzyl)amino)propan-2-yl)-2-methylbenzamide (5q)

The title compound was prepared following general procedures B: white solid. 1H NMR (DMSO-$d_6$, 400 MHz) δ: 7.57 (d, J=8.0 Hz, 3H), 7.42 (d, J=6.7 Hz, 1H), 7.29 (d, J=7.9 Hz, 2H), 7.15 (m, 2H), 7.10 (d, J=8.2 Hz, 2H), 6.72 (d, J=8.2 Hz, 2H) 4.77 (t, J=7.9 Hz, 1H), 4.43 (q, J=8.2 Hz, 2H), 2.99 (m, 2H), 2.21 (s, 3H). $^{13}$C NMR (100 MHz, DMSO-$d_6$) δ: 172.1, 167.5, 155.2, 141.2, 136.8, 134.4, 132.9, 132.1, 129.2, 129.0, 128.5, 127.2, 125.5, 124.9, 124.1, 115.8, 57.8, 43.6, 37.5, 17.2.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulation of the various compounds and compositions described herein, the methods described herein or in the steps or the sequence of steps of the methods described herein without departing from the spirit and scope of the present disclosure. All patents, published patent applications, and non-patent publications referenced in any portion of this application are herein expressly incorporated by reference in their entirety to the same extent as if each individual patent or publication was specifically and individually indicated to be incorporated by reference.

What is claimed is:

1. A compound having a formula as represented by chemical structure I:

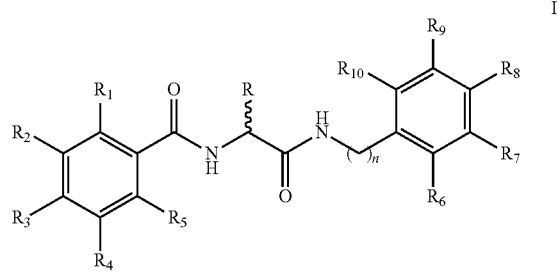

wherein:
R=H, Alkyl, or Phenyl;
$R_1$=H, Me, Cl, F, OMe, OH, or Phenyl;
$R_2$=H or OH;
$R_3$=H, $NH_2$, Me, Cl, F, OMe, OH, or Phenyl;
$R_4$=H or OH;
$R_5$=H, Me, Cl, F, OMe, or OH;
$R_6$=H, Me, Cl, F, OMe, OH, $CCl_3$, or $CF_3$;
$R_7$=H, Me, Cl, F, OMe, OH, or Piperonyl;
$R_8$=$CCl_3$, $CF_3$, or Piperonyl;
$R_9$=H, Me, Cl, F, or OMe;
$R_{10}$=H, Me, Cl, F, OMe, OH, $CCl_3$, or $CF_3$; and
n=1, and
wherein one of $R_2$ and $R_4$=H, and one of $R_2$ and $R_4$=OH.

2. The compound of claim 1, wherein R, $R_1$, $R_3$, $R_4$, $R_5$, $R_6$, $R_7$, $R_9$, and $R_{10}$=H, $R_2$=OH, and $R_8$=$CF_3$.

3. The compound of claim 1, wherein R, $R_1$, $R_2$, $R_3$, $R_5$, $R_6$, $R_7$, $R_9$, and $R_{10}$=H, $R_4$=OH, and $R_8$=$CF_3$.

4. A composition comprising the compound of claim 1 disposed in a pharmaceutically-acceptable carrier, diluent or vehicle.

* * * * *